United States Patent [19]
Grettner

[11] Patent Number: 5,848,956
[45] Date of Patent: Dec. 15, 1998

[54] MULTI-PURPOSE LAT SLING

[76] Inventor: Norman L. Grettner, 66 Mack Dr., Las Vegas, Nev. 89115-1910

[21] Appl. No.: 820,713

[22] Filed: Mar. 18, 1997

[51] Int. Cl.$^6$ ........................................................ A61F 5/02
[52] U.S. Cl. .............................. 482/69; 482/140; 602/18
[58] Field of Search ............................. 482/74, 142, 125, 482/140, 907, 69; 128/874–878; 602/18

[56] References Cited

U.S. PATENT DOCUMENTS

| | | |
|---|---|---|
| 3,815,588 | 6/1974 | Klausnier . |
| 4,285,337 | 8/1981 | Cosentino . |
| 4,335,875 | 6/1982 | Elkin . |
| 4,570,929 | 2/1986 | Shoemaker . |
| 4,625,719 | 12/1986 | Chambers . |
| 4,759,353 | 7/1988 | Melendez . |
| 4,763,894 | 8/1988 | Barrett . |
| 5,001,791 | 3/1991 | Toso . |
| 5,086,762 | 2/1992 | Chee . |
| 5,295,949 | 3/1994 | Hathaway . |
| 5,549,121 | 8/1996 | Vinci . |

OTHER PUBLICATIONS

Magazine Photo p. 61 of Natural Bodybuilding and Fitness Nov. 1996, vol. 9, No. 4.

*Primary Examiner*—Jerome Donnelly

[57] ABSTRACT

Disclosed is a multi-purpose lat sling (61), which can be used to exercise and develop the latissimus dorsi, triceps, and abdominal muscles of the human body. It is comprised of a lat sling (42), having a connective band (25) separating a uniform pair of loops (26), a pair of U-shaped forearm belts (34), and a pair of assemblies, each comprised of an inner shell (50) and an outer skin (57). Sling (61) is attached via releasable surface means to a standard lat-bar, or typical pull-bar, and suspended therefrom. To exercise the latissimus dorsi, a user places each forearm through its respective loop (26). With forearm flexed, a portion of user's arm-elbow-forearm resides within shell (50) and skin (57) assembly. With both appendages thus encased, and resistance against the back of each upper arm, the user can then begin exercise by extending or adducting the arm. Sling (61) provides considerable user-convenient surface portions as means with which to releasably grip sling (61) in order to perform a variety of exercises. Each assembly also provides surfaces suitable for the inclusion of a pocket (56).

9 Claims, 4 Drawing Sheets

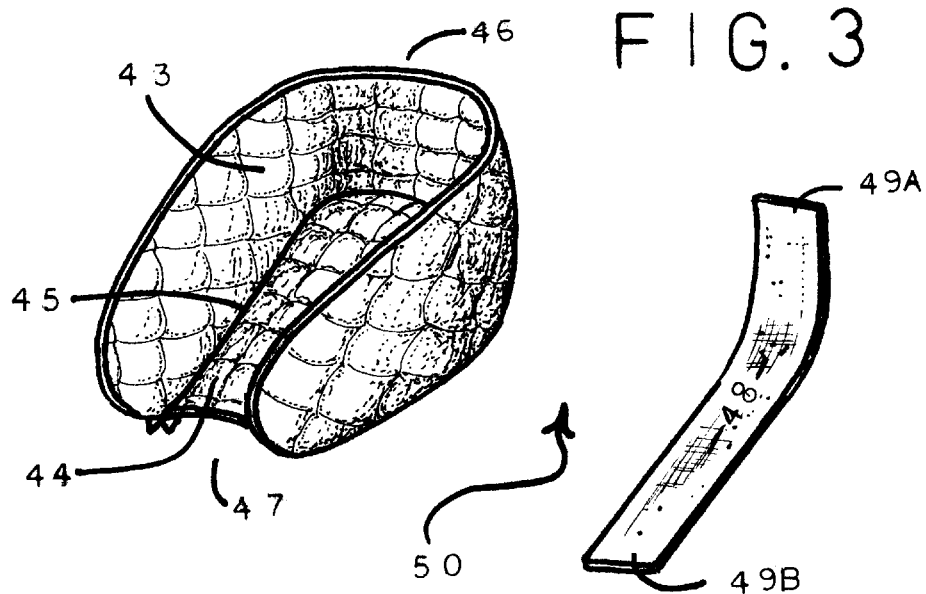
FIG. 3
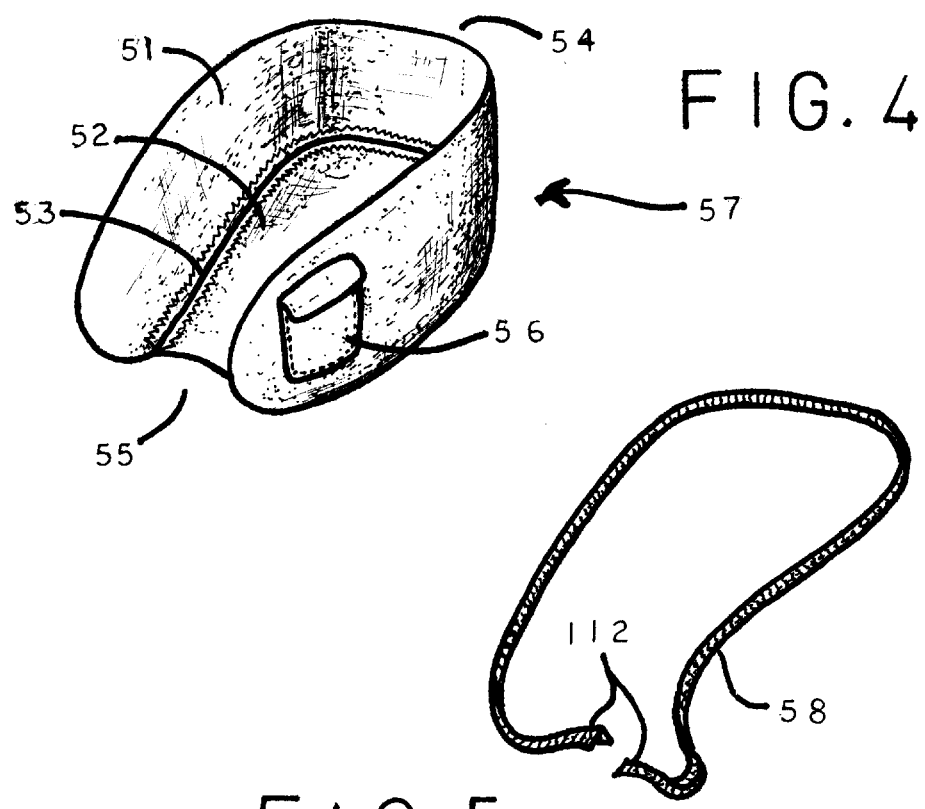
FIG. 4
FIG. 5

MULTI-PURPOSE LAT SLING

BACKGROUND—FIELD OF INVENTION

The present invention relates to an exercise sling, specifically to an improved sling which may be used by an exerciser to develop the latissimus dorsi, triceps, and abdominal muscles of the human body.

DISCUSSION OF PRIOR ART

There has been a variety of arm slings available for a number of years. Most of these are designed to immobilize or stabilize a patient's arm during healing. One sling, however, U.S. Pat. No. 4,763,894 to Barrett, 1988 Aug. 16, is made for swinging movements but requires the addition of overhead support. While cradled swinging does provide some exercise, it does not target or "isolate" the principal muscle of the middle-back, latissimus dorsi, for development. Also, entry into the apparatus is cumbersome. For a handicapped person, or therapy patient, considerable assistance may be required.

Another sling of prior art is made to support the body-weight of a user during leg-lift exercise. This apparatus requires that two separate slings be used, each suspended from and spaced apart on a specially-constructed lateral support bar. While this sling is touted as a developer of the abdominal muscles, it does not permit flexion of the upper body in order to do so. Instead, it targets two small muscles of the pelvis, psoas major and psoas minor. These muscles act to raise the knees toward the chest, a movement which, if the back is arched while flexing the pelvis, can result in serious damage to the lumbar region of the spine. It also does not permit lateral flexion of the trunk in order to develop the oblique muscles of the abdomen. In particular, however, by restricting upper arm movement, this sling prohibits arm extension and arm adduction, two movements about the shoulder-joint which are absolutely essential for full development of latissimus dorsi, hereafter referred to as the lats.

Standard methods of lat development are extension movements that involve the biceps brachii muscle of the upper arm and the large, powerful lat muscle of the middle-back. When performing lat exercises, such as Chins or Lat Pulldowns, for instance, the biceps contract to flex the arm, bending it at the elbow, while the lats contract to pull the upper arm down. The major problem encountered, however, is that the smaller and weaker biceps usually tire and fail before the lats have been thoroughly worked. To effectively target the lats, then, the exerciser should place the resistance against the back of the upper arms, just above the elbows. By disinvolving the biceps, all the stress is transferred onto the lats, where it should be.

Traditionally, machines that accommodate lat exercise are of the cable-and-pulley variety. However, these machines require considerable bicep involvement. This major disadvantage even extends to "home" gyms, such as the multi-station and "rider" types. In recent years, though, some of the large cam-type back machines have found their way into commercial gyms. While these machines accurately target the lats, they are often difficult to set-up, that is, to adjust quickly and easily to accommodate the wide disparity in body configurations. Because these machines are also bulky and somewhat confusing in appearance, they can be intimidating to smaller, beginning bodybuilders. They are expensive, too, contributing to a shortage in some gyms. Due to such scarcity, athletes who do favor their use often find themselves standing idle while awaiting their turn to exercise. This interruption in a bodybuilder's routine can disrupt exercise sequencing and affect cardio-vascular pulse-rate level. They are limited in function as well, requiring that two machines be used to effectively work the lats; one to extend the arm, and another to adduct it.

Recently, some manufacturers of lat bars have reduced the length of the bar to general shoulder-width, making it a tool for developing the triceps muscle at the back of the upper arm. A drawback of this design, though, is that it requires the exerciser use a pronated or palms-down grip, which stresses the inner head of the triceps. Since most athletes, particularly bodybuilders, want to look wider, the outer head should be targeted. For this purpose, the bodybuilder needs to use a neutral or palms-facing grip.

Accordingly, the known prior art cited above are limited in their functions and the present invention addresses the desirability of providing a multi-purpose lat sling.

OBJECTS AND ADVANTAGES

It is therefore a primary object to provide a multi-purpose lat sling having several useful health and exercise functions, some of which are:

(a) to provide a sling which permits lat muscle development by allowing resistance to be placed against the back of the upper arms, just above the elbows;

(b) to provide a sling which permits lat development by allowing extension and adduction of the arm;

(c) to provide a sling having suitable gripping surfaces that accommodate a neutral or palms-facing grip in order to perform triceps muscle exercise;

(d) to provide a sling having suitable gripping surfaces that accommodate the performance of abdominal muscle exercise;

(h) to provide a sling that allows a user exhibiting less lat development on one side of the body to emphasize exercise for that lagging muscle part;

(j) to provide a sling that virtually eliminates biceps involvement, thereby permitting greater lat development in less time;

(l) to provide a sling that can be beneficial to a physical therapy patient, and, particularly, to a person having the use of only one forearm;

(w) to provide a sling that accommodates exercise without assistance by a partner;

(x) to provide a sling that accommodates different body heights;

(y) to provide a sling that can accommodate considerable weight-resistance;

(z) to provide a sling that is lightweight and portable.

The construction and method of operation of the present invention, however, together with additional objects and advantages thereof, will be best understood from the following description of specific embodiments when read in conjunction with accompanying drawings.

BRIEF DESCRIPTION OF DRAWINGS

FIG. 3 is a rear perspective view of elements of an arm-elbow inner shell of an embodiment of my invention showing the overall construction thereof;

FIG. 4 is a rear perspective view of an arm-elbow outer skin of an embodiment of my invention showing the overall construction thereof;

FIG. 5 is a perspective view of the edge-binding element of my invention;

LIST OF REFERENCE NUMERALS

| | | | |
|---|---|---|---|
| 20 | webbing strap | 22 | distal ends |
| 24 | stitch engagement | 25 | connective band |
| 26 | sling loop | 28 | lateral walls |
| 30 | lowermost bight | 32 | lat sling embodiment |
| 34 | forearm belt | 36 | distal end |
| 38 | stitch engagement | 40 | gap |
| 41 | passage | 42 | lat sling embodiment |
| 43 | inner shell side-panel | 44 | inner shell bottom |
| 45 | inner shell seam | 46 | closed end |
| 47 | open end | 48 | arm-elbow strap |
| 49 | distal end | 50 | inner shell |
| 51 | outer skin side-panel | 52 | outer skin bottom |
| 53 | outer skin seam | 54 | closed end |
| 55 | open end | 56 | pocket |
| 57 | outer skin | 58 | edge-binding |
| 59 | stitch engagement | 60 | stitch engagement |
| 61 | lat sling embodiment | 112 | distal ends |

SUMMARY

The present invention recites a multi-purpose lat sling having several useful health and exercise functions.

DESCRIPTION OF INVENTION

Figure 1:
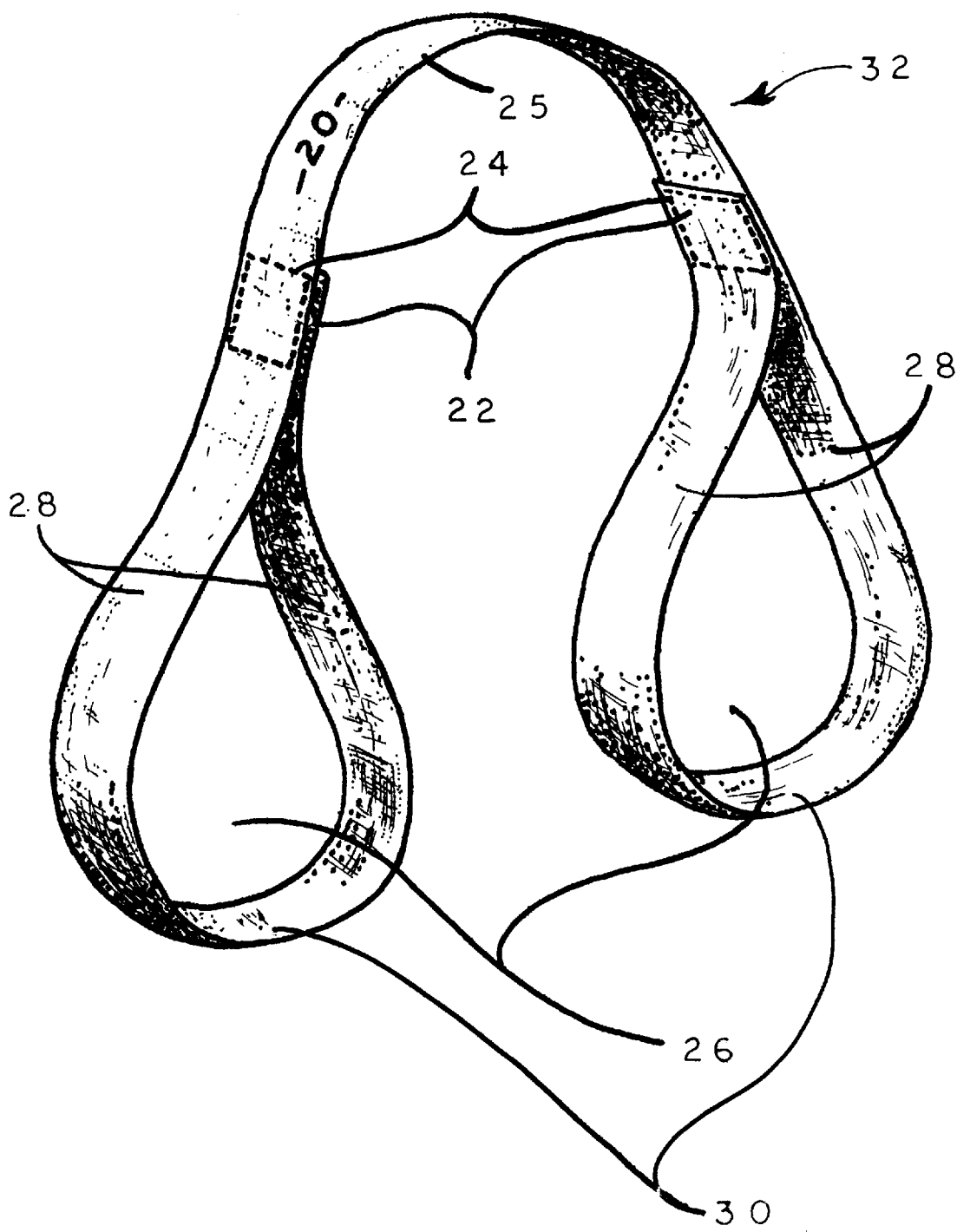
FIG. 1 is a perspective view of an embodiment of my invention showing the overall construction thereof.

Referring now in detail to the drawings in which like characters refer to like elements throughout the various drawings, FIG. 1 illustrates an embodiment in which a multi-purpose lat sling 32 is comprised of a webbing strap 20 having a pair of distal ends 22, stitch engagement 24, a connective band 25, a pair of loops 26, each having a pair of lateral walls 28 and a lowermost bight 30.

Strap 20 is shown as a substantially elongated element, preferably constructed of woven fabric, such as seat-belt webbing or like-material. It should be flexible, non-elastic, and of suitable strength and dimensions.

A substantial portion of each distal end 22 is folded laterally back upon itself proximal to the same-side surface as its opposite end 22. Each end 22 is attached by stitch engagement 24 to strap 20 at a pre-determined location substantially distal of the substantial middle of strap 20, thereby describing a connective band 25 separating a substantially uniform pair of sling loops 26, each having an inner and an outer surface that comprise substantial lateral walls 28 and lowermost bight 30.

To obtain greater thickness, an optional piece of felt (not shown) or cloth-covered foam material (not shown) may be attached to a portion of either surface of sling 32. The dimensions of this piece would correspond in length and width as that of the portion of sling 32.

Figure 2:
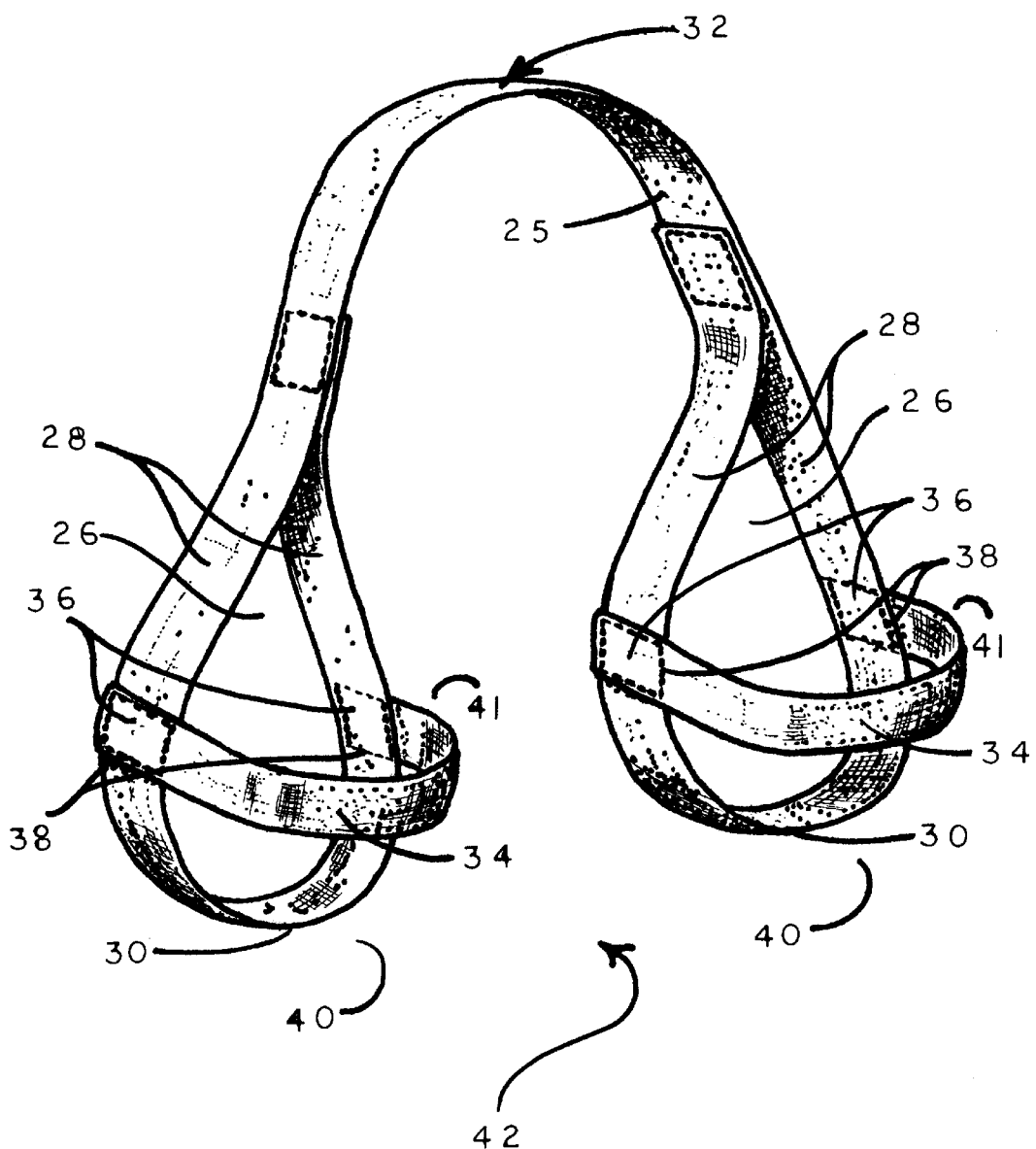
FIG. 2 is a front perspective view of an embodiment of my invention showing the overall construction thereof.

FIG. 2 illustrates an embodiment in which a multi-purpose lat sling 42 is comprised of a lat sling 32, a pair of forearm support braces or belts 34, a pair of distal ends 36, stitch engagement 38, a pair of arm-elbow gaps 40, and a pair of arm passages 41.

Lat sling 32, as previously shown in FIG. 1, is an embodiment of a multi-purpose lat sling comprised of a connective band 25 separating a substantially uniform pair of sling loops 26, each having an inner and an outer surface that comprise substantial lateral walls 28 and lowermost bight 30.

Belt 34 is a substantially elongated element having a pair of distal ends 36. It is preferably constructed of woven fabric, such as seat-belt webbing or like-material. Belt 34 should be flexible, non-elastic, and of suitable strength and dimensions.

Each belt 34, being identical to the other, is attached at each of its ends 36 by stitch engagement 38 to respective pre-determined locations on the outer surfaces of walls 28, and extends substantially lateral therefrom to describe a U-shaped structure separating a gap 40 below of substantial area from a passage 41 above of substantial area.

FIGS. 3 to 6 illustrate a preferred embodiment in which a multi-purpose lat sling 61 is comprised of a lat sling 42, a pair of inner shells 50, a pair of outer skins 57, edge-binding 58, stitch engagement 59, and stitch engagement 60.

Lat sling 42, as previously shown in FIG. 2, is, by itself, an embodiment of a multi-purpose lat sling. However, in the preferred embodiment it represents only part of an expanded support structure. Sling 42 is comprised of a connective band 25 separating a substantially uniform pair of loops 26, each having an inner and an outer surface that comprise substantial lateral walls 28 and lowermost bight 30, and a pair of forearm belts 34, each attached to its respective loop 26 to form a U-shaped structure separating a gap 40 below of substantial area from a passage 41 above of substantial area.

FIG. 3 illustrates a group of elements that, together, form an inner shell 50, which is comprised of an inner shell side-panel 43, an inner shell bottom 44, an inner shell seam 45, a closed end 46, an open end 47, and an arm-elbow support strap 48 having a pair of distal ends 49A and 49B.

Panel 43 and bottom 44 are preferably constructed of the same padded or quilted cloth material, such as cotton or cotton-blends, although other cloth materials and finishes are suitable. Panel 43 and bottom 44 are cut to pattern and, positioned right-side to right-side to produce a finished seam, joined together by stitch engagement along inner seam 45, thereby forming a channel-structure having a first or closed end 46 opposite a second or open end 47.

Strap 48 is a substantially elongated element, preferably constructed of woven fabric, such as seat-belt webbing or like-material. It should be flexible, non-elastic, and of suitable strength and dimensions.

Strap 48 has a dimensional length corresponding with that of the length of bottom 44 combined with the height of end 46 (height of end 46 being the width minus a predetermined seam 45 allowance of the substantial middle of panel 43). Strap 48 is positioned longitudinally and centrally along the length of the underside surface of bottom 44 and centrally along the height of end 46. Strap 48 is joined by stitch engagement (not shown) to bottom 44 and end 46.

FIG. 4 shows an outer skin 57 that is comprised of an outer skin side-panel 51, an outer skin bottom 52, an outer skin seam 53, a closed end 54, an open end 55, and a pocket 56.

Panel 51 and bottom 52 are preferably constructed of the same material, such as cotton, cotton-blends, denim, or nylon, although other materials may be used. Panel 51 and bottom 52 are cut to pattern and, positioned right-side to right-side, joined together by stitch engagement along outer skin seam 53, and turned right-side out, thereby forming a channel-structure having a first or closed end 54 opposite a second or open end 55.

Pocket 56 is preferably constructed of the same material as panel 42, though other materials may be used. The configuration and method of construction of pocket 56 is optional, as is its location, or inclusion. For instance, it may be constructed as a pouch and attached to the inner wall of panel 51 rather than sewn to the outer surface, as shown. Though illustrated as a single element, a plurality of pockets 56 are possible.

FIG. 5 illustrates edge-binding 58 as a substantially elongated element having a pair of distal ends 112, and preferably constructed of suitable binding material, such as quilt binding, strapping, or cording. There are a variety of binding materials commercially available, accessible in assorted colors, finishes, and dimensions.

With shell 50 positioned uniformly within skin 57, binding 58 clasps a substantial portion of the perimeter edges of shell 50 and skin 57. Attachment of shell 50 to skin 57 is by stitch engagement (not shown) along and proximal to the lower edges of binding 58. For best appearance, it is preferable that ends 112 are positioned and overlap at the middle of open ends 44 and 55.

Optional stitching (not shown) that would further secure shell 50 to skin 57 may be added proximal to and parallelly along both sides of seam 53, thereby engaging corresponding portions of shell 50 as well as the free edges of seams 53 and 45.

Figure 6:
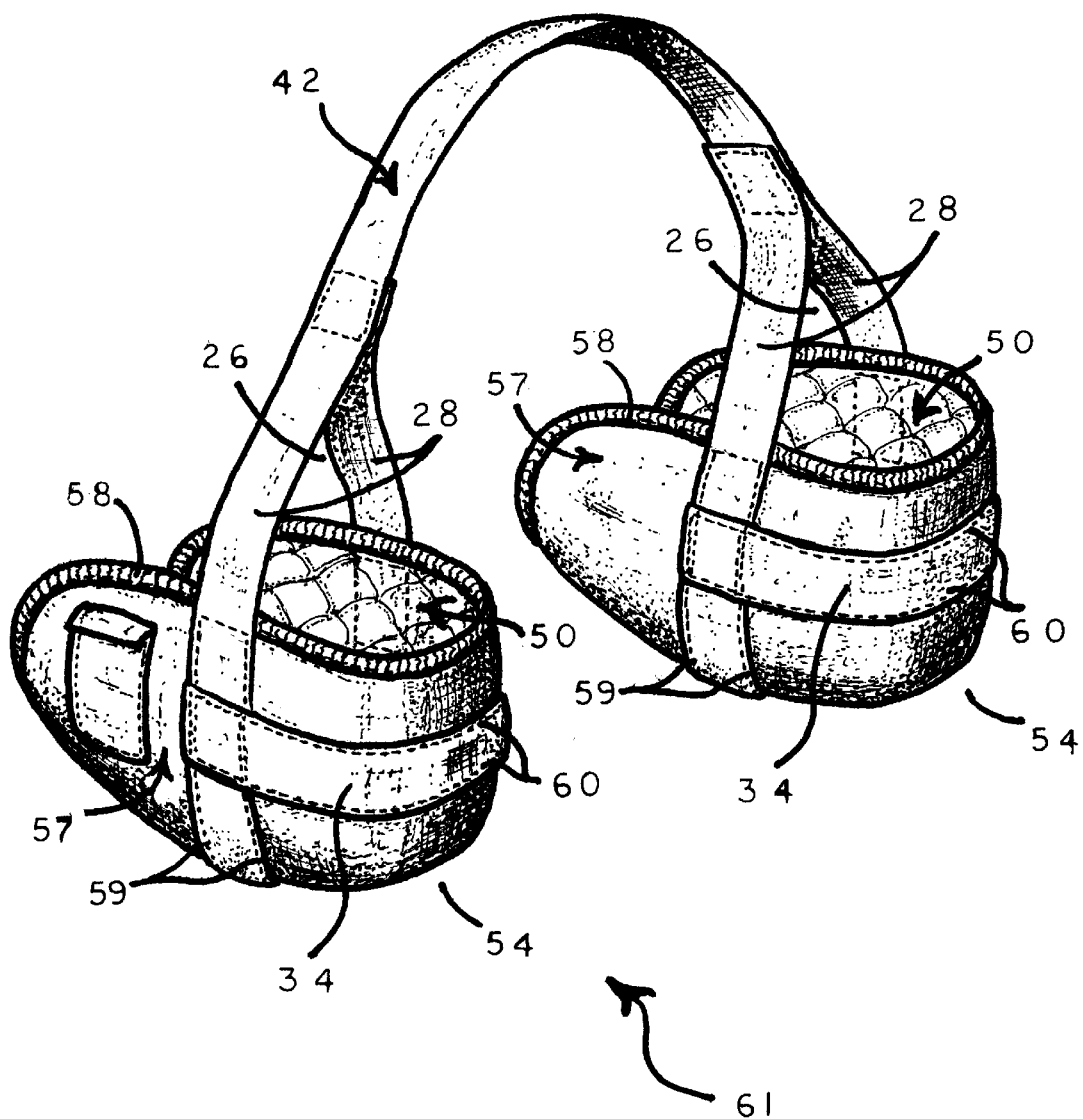
FIG. 6 is a front perspective view of the preferred embodiment of my invention showing the overall construction thereof.

FIG. 6 is a front perspective view of the preferred embodiment of a multi-purpose lat sling 61 showing the overall construction thereof.

Facing in the same direction, each pair of corresponding shell 50 and skin 57 assemblies is positioned uniformly within the girth of its corresponding loop 26, and proximal to the inner surfaces of walls 28, bight 30 (not shown), and belt 34. Walls 28 and bight 30 are situated substantially central about the lateral sides of skin 57 and corresponding portion of bottom 52 (not shown). Belt 34 is positioned lengthwise about end 54, and substantially central between the top edge and lower border of end 54, and substantially parallel with the top edge of end 54. Each pair of shell 50 and skin 57 assemblies is attached by stitch engagements 59 and 60 to corresponding portions of each pair of corresponding walls 28 and each corresponding strap 34.

OPERATION OF INVENTION

FIG. 1 Briefly described, lat sling 32 is comprised of a webbing strap 20 having a pair of distal ends 22 that are folded back upon themselves and secured to strap 20 to form a connective band 25 separating a pair of loops 26, each having a pair of lateral walls 28 and lowermost bight 30.

The manner in which sling 32 is used is by first attaching it to a lat bar (a lat bar is a length of bar suspended horizontally from overhead by a cable, which is secured at its other end to a stack of weights). This is done by draping sling 32 around the cable and over the opposite side of the bar, with the bottom of each loop 26 at the same height above the floor. The length of sling 32 can be adjusted to suit a taller person by wrapping band 25 around the cable as many times as needed.

The user places each arm through a corresponding loop 26, with bight 30 at the back of the upper arm, just above the elbow, and walls 28 about the sides of the arm. With the forearm flexed vertically at an approximate right angle with the upper arm, the user grips a portion of corresponding loop 26, or, depending upon the length of the user's forearm, a corresponding portion of band 25. If preferred, the length of sling 32 can be adjusted so that some portion of the user's hand remains in close contact with the lat bar to act as a tracking guide. The user, then seated, begins a lat exercise by pulling downward from overhead, extending the arms. Though some assistance by the biceps and forearm muscles may be provided, it is minimal because they are not allowed to fully contract, only tense, thereby transferring a substantial majority of the stress onto the lats. Sling 32 is ideally suited to an exerciser with less lat development on one side of the body because stress can be easily shifted to the weaker muscle-part by exerting less effort by the stronger side. This exercise may also be performed by adducting the arms, that is, by pulling downward from overhead laterally. To conclude a "pulldown" exercise, the user simply allows the bar to return to its overhead starting position.

To use sling 32 as a developer of the triceps muscles, sling 32 is first attached, as in previous fashion, to a lat bar or an appropriate triceps bar. However, the user's grip differs dramatically from that used with a traditional lat or triceps bar. With sling 32, an exerciser is allowed to use a neutral or palms-facing grip, which shifts the majority of the stress onto the lateral or outside head (which displays best) of the triceps. From a standing position, the user grasps sling 32 at, or slightly above, eye level, with each hand gripping a corresponding portion of sling 32. With the elbows several inches in front of the body and approximately shoulder-width apart, the user begins the exercise by extending only the forearms. The elbows should not be allowed to move from in front of the body. To conclude the exercise, the user simply allows the bar to return to its overhead starting position.

To perform abdominal exercises with sling 32, it is best that they be performed from a kneeling position, with buttocks resting on the heels. With sling 32 attached, as previously described, to a lat bar, the user reaches overhead and grasps sling 32 securely with both hands and pulls it to the forehead, or along each side of the head. With sling 32 held firmly in this manner throughout the exercise, the user flexes the spine or "crunches" the abdominals, bringing the head toward the front of the knees. To target the oblique muscles at the sides of the abdomen, the trunk is flexed laterally, twisting the upper body and bringing the head to a position outside the knees. For even development of the obliques, the trunk is flexed to the opposite side of the knees with the next repetition. To conclude either version of trunk-flexion exercise, the user simply allows the bar to return to its overhead starting position.

Any of the above described exercises can be safely performed by a person having the use of only one forearm. However, a well-secured grip is necessary, and a different stance or shift in body position is usually required.

FIG. 2 Briefly described, lat sling 42 is identical to sling 32, with the exception of an added pair of U-shaped belts 34. Each belt 34 is attached at the front of its respective loop 26 and extends laterally therefrom, separating a gap 40 below from a passage 41 above.

Sling 42 is attached to a lat bar in the same manner as sling 32. The user then places the forearm through loop 26 and passage 41. The forearm is flexed at an approximate right angle with the upper arm, and the elbow is positioned within gap 40, with bight 30 at the back of the upper arm, just above the elbow, and lateral walls 28 about the sides of the arm. With the forearm flexed and braced against belt 34, the user can grasp a portion of loop 26, or a portion of band 25. All the exercises described in FIG. 1 can be performed in virtually the same manner as with sling 32. However, because the forearm is braced against belt 34, and the elbow portion of the arm is secured within gap 40, arm-elbow leverage is substantially increased during the performance of a lat-pulldown exercise.

FIG. 6 Briefly described, lat sling 61 is the preferred embodiment of a multi-purpose lat sling. It is identical to sling 42, but with improvements that include a pair of inner shells 50 joined with a corresponding pair of outer skins 57 to form a virtually identical pair of assemblies that provide greater arm-elbow stability and support, increased comfort, and heightened attractiveness. Each assembly is secured along its perimeter edge by stitched edge-binding 58. Characteristic of each assembly is a comfortably padded interior and an attractive exterior, the latter including a pocket 56 for convenient storage of valuables. Each assembly features a channel-structure that has a closed portion about the front that is comprised of closed end 46 as an inner surface and closed end 54 as an outer surface. Each closed end 46 and 54 is opposite an unenclosed portion of the assembly that is comprised of open end 47 as an inner surface and open end 55 as an outer surface. Each assembly is mounted uniformly within its respective loop 26 and belt 34, and joined by stitch engagements 59 and 60 to corresponding portions of sling 42.

To use sling 61, it is first attached to a lat bar in the same manner as that of slings 32 and 42. The arm-elbow is positioned within each assembly in the same way as is done with sling 42. However, gap 40 is now enclosed by a strong wall of fabric and a portion of strap 48. The back and sides of the upper arm receive greater support due to the combined strength of the lateral walls of panels 43 and 51 and bottoms 44 and 52. Lat-pulldowns are executed in the same manner as with slings 32 and 42, although, by using sling 61, the biceps and forearm muscles can be relaxed considerably. With substantial portions of the upper arm and forearm, and all of the elbow, thus encased, the user can focus greater concentration upon exercise performance, apply more effort, and, therefore, achieve faster and better results.

Using sling 61, performance of triceps and abdominal exercises are done in virtually the same manner as when using either sling 32 or sling 42.

CONCLUSION, RAMIFICATIONS, AND SCOPE OF INVENTION

Thus the reader will see that the multi-purpose lat sling of the invention provides a convenient, easily accessible, aesthetically pleasing, lightweight and portable, versatile, and safe multi-functional exercise sling that can be used by responsible persons of almost any age.

While my above description contains many specificities, these should not be construed as limitations on the scope of the invention, but rather as an exemplification of one preferred embodiment thereof. Many other variations are possible. For example, sling 32 can be constructed of a heavy, tufted cotton so that it can also function as a work-out towel. Many commercial gyms require that all members keep one in their possession at all times while using the facility. Sling 42 could have a strap similar to strap 48 that is attached at one of its ends 49 to bight 30, and at its other end 49 to belt 34, thereby providing greater arm-elbow-forearm support. The shell assemblies of sling 61 could be constructed of one-piece rigid or semi-rigid foam or plastic material. The use of rivets as a fastening method would be appropriate in the construction of any of the above described embodiments.

Accordingly, the scope of the invention should be determined not by the embodiment(s) illustrated, but by the appended claims and their legal equivalents.

I claim:

1. A multi-purpose lat sling kit for exercising comprising:
   a substantially elongated strap made of flexible, non-elastic material having a pair of distal ends, whereof each said distal end is folded laterally upon itself and secured to said strap at a pre-determined location;
   thereby forming a connective band separating a substantially uniform pair of loops, each said loop having an inner and an outer surface comprising a pair of substantial lateral walls and a lowermost bight;
   and a pair of forearm belts, each said belt comprising a substantially elongated element having pre-determined dimensions and an inner and an outer surface, and a pair of distal ends;
   wherein each said end of said element is attached at a respective pre-determined location to a respective said lateral wall of respective said loop, and said belt extending substantially lateral therefrom to describe a U-shaped structure separating a passage above of substantial area from a gap below of substantial area;
   said kit further including a substantially uniform pair of assemblies, each said assembly comprising;
   a pair of side-panels having pre-determined dimensions, and joined to a bottom with panel having pre-determined dimensions;
   thereby describing a substantially U-shaped channel-structure having a closed end opposite and open end;
   attachment means for affixing each said assembly to a respective portion of said multi-purpose lat sling;
   whereby a said substantial portion of said user's said arm, elbow and forearm may be accommodated while accomplishing said variety of exercises.

2. The multi-purpose lat sling of claim 1 wherein said strap is constructed of woven material, such as seat-belt webbing.

3. The multi-purpose lat sling of claim 1 wherein the substantial middle of said band has as one of its functions engagement means to releasably cooperate with a pre-determined portion of a conventional exercise pull-bar so as to enable said band and said pair of said loops to hang suspended therefrom.

4. The multi-purpose lat sling of claim 1 wherein said panels and said bottom are constructed of the same material.

5. The multi-purpose lat sling of claim 4 wherein said material is padded cloth.

6. The multi-purpose lat sling of claim 1 wherein said attachment means is stitch engagement.

7. The multi-purpose lat sling of claim 1 wherein said attachment means is stitch engagement.

8. The multi-purpose lat sling of claim 1 wherein the substantially medial portion of said band is adapted to releasably cooperate with a pre-determined portion of a conventional lat or triceps bar so as to enable said band to hang suspended therefrom.

9. The multi-purpose lat sling of claim 1 wherein said belts are constructed of the same material as said strap.

* * * * *